United States Patent [19]
Tibbetts et al.

[11] Patent Number: 4,919,838
[45] Date of Patent: Apr. 24, 1990

[54] BAR SHAMPOO AND SKIN SOAP

[75] Inventors: Hubert M. Tibbetts, 137 Pecksland Rd., Greenwich, Conn. 06830; Mukat Gupta, South Burlington, Vt.

[73] Assignee: Hubert M. Tibbetts, Greenwich, Conn.

[21] Appl. No.: 252,167

[22] Filed: Sep. 30, 1988

[51] Int. Cl.$^5$ .................. C11D 9/00; C11D 15/00; A61K 7/06
[52] U.S. Cl. .................. 252/117; 252/108; 252/134; 252/DIG. 5; 252/DIG. 13; 252/DIG. 16; 424/70
[58] Field of Search ........ 252/108, DIG. 16, DIG. 5, 252/117, 134, DIG. 13; 424/70

[56] References Cited

U.S. PATENT DOCUMENTS

| | | | |
|---|---|---|---|
| 2,527,076 | 10/1950 | Preston | 252/117 |
| 2,607,740 | 8/1952 | Vitale et al. | 252/550 |
| 3,852,211 | 12/1974 | Ohren | 252/110 |
| 4,012,341 | 3/1977 | Orshitzer | 252/DIG. 13 |
| 4,100,097 | 7/1978 | O'Roark | 252/DIG. 16 |
| 4,695,395 | 9/1987 | Caswell et al. | 252/DIG. 16 |

Primary Examiner—Prince E. Willis
Assistant Examiner—John F. McNally
Attorney, Agent, or Firm—Parmelee, Bollinger & Bramblett

[57] ABSTRACT

A bar composition which is useful both as a shampoo for hair or scalp and as a cleansing soap for the skin or body and which preferably contains hair and skin conditioners. The bar product will remove surface grease, dirt, skin debris and natural skin secretions from the hair shaft or scalp without removing excessive amounts of oil and without leaving a soap residue on the hair or scalp and yet functions effectively as a skin or body cleaning soap with sufficient lathering and cleaning action for both body and hair.

28 Claims, No Drawings

BAR SHAMPOO AND SKIN SOAP

FIELD OF THE INVENTION

This invention relates to a composition which can be shaped or formed into a bar, cake or other solid product useful both as a shampoo for the hair and scalp and also as a soap for the skin or body. More particularly, this invention relates to such a solid product that is useful as a shampoo, with conditioners for the hair and scalp, and also as a soap for the skin or body with skin conditioners.

BACKGROUND OF THE INVENTION

Cake soap has been used time immemorial as a product for body cleanliness and personal hygiene and over the years many improvements have been made to such cake soap products to enable one to more effectively and efficiently clean the body or skin of the user. Such cake soap products were primarily produced from saponified animal and vegetable fats and oils.

Originally, shampoos for the hair or scalp were made from soap or mixtures of soaps. However, such shampoos were not readily accepted and used for a number of reasons including the highly undesirable poor lathering and their tendency to form a lime soap deposit, residue or film on the hair or scalp, particularly in hard-water areas, by way of the formation of insoluble calcium and magnesium salts due to the presence of carboxylic groups linked to long-chain hydrocarbons. For the most part, use of such cake soaps as shampoos has been abandoned except in "emergency" type situations where the user is without a shampoo and cleansing of the hair is an "immediate necessity".

Due to the aforesaid drawbacks, special shampoo products for the hair and scalp were formulated. These shampoo products have been in the form of clear or opaque liquids, lotions, pastes, gels, aerosols and dry absorbent powder products. For the most part, these shampoos are now produced from synthetic detergents. The shampoo products have been produced in the aforesaid forms but have not been available commercially in acceptable form in solid bar or cake form. Cake or bar soaps which have been available for use in cleansing the skin or body have not been useful as shampoos, particularly as shampoos having hair conditioning properties, due to the undesirable residue or deposit left on the hair or scalp when such bar soap is attempted to be used as a shampoo medium.

It is therefore highly desirable to provide a composition that can be formed into a solid bar or cake and which is useful both as a shampoo for the hair or scalp and also as a cleansing soap for the skin or body. It is also desirable that such a composition be provided which will remove surface grease, dirt, skin debris and natural skin secretions from the hair shaft or scalp without leaving a soap residue on the hair or scalp and yet functions effectively as a skin or body cleansing soap with sufficient lathering and cleansing action for both body and hair. It is a further object of this invention to provide such a solid shampoo and soap product which contains hair conditioning agents.

SUMMARY OF THE INVENTION

It has been discovered that a solid bar or cake product which is useful and effective both as a shampoo for the hair or scalp and as a cleansing soap for the body or skin can be provided by a composition comprising a natural soap base or a mixture of a natural soap base and a synthetic detergent soap base with the proviso that the composition contains (A) disodium lauryl sulfosuccinate, sodium cocyl isethionate or sodium lauryl sulfate, and (B) cocoamide MEA, cocoamide DEA or lauramide DEA in a weight ratio of about 3 parts component (A) to 2 parts component (B) and the amount of component (A) present in the composition is from about 3 to about 15% by weight of the total composition and the amount of component (B) present in the composition is from about 2 to about 10% by weight of the total composition. In a preferred form, the composition of this invention will also have present one or more of the following classes of ingredients: hair conditioning agents, skin conditioning agents, hair reoiling agents, chelating or sequestering agents and, if desired, antioxidants or preservatives, dyes or coloring agents and fragrances and the like.

DETAILED DESCRIPTION OF THE INVENTION

A bar or cake product which is useful both as a shampoo for the hair or scalp and as a cleansing soap for the skin or body is provided by a composition containing a natural soap base or a mixture of a natural soap base and a synthetic detergent soap base. Any suitable natural soap base can be employed. The natural soap base is a mixture of salts of fatty acids which are generally obtained by saponifying animal and vegetable fats and oils with alkalis such as sodium or potassium hydroxide or alkanolamines such as ethanolamine or the like. It is generally preferred, according to this invention, that the natural soap base employed be primarily saponified coconut oil.

The synthetic soap detergents base that can be employed in combination with the natural soap base may be any suitable synthetic detergent soap but is preferably an anionic or nonionic based synthetic detergent composition. As examples of synthetic detergent soap base formulations that may be employed with the natural soap base there may be mentioned detergent formulation based on anionics such as alkyl benzene sulfonates, alkyl sulfates, alkyl benzene polyoxyethylene sulfonates, sulfated monoglycerides and alcohol ether sulfates or based on nonionics surfactants such as those obtained by condensation of alkylene oxide groups with organic hydrophobic compounds having an active hydrogen such as those nonionic identified as Pluronics, Igepals or Tweens, for example, Pluronic F-68 and Tween 80. As an example of a suitable synthetic detergent soap base there can be mentioned a formulation containing sodium lauryl sulfate, disodium monolauryl sulfosuccinate, cetearyl alcohol, corn starch, sodium sulfate and water.

While the composition of this invention may be based on a natural soap base alone, it is to be understood that the composition of the soap base may comprise a mixture of natural soap base and a synthetic detergent soap base in an amount of up to about 60% of synthetic detergent soap base based on the combined weight of the natural and synthetic soap bases. Thus, the soap base may comprise from about 40 to 100% by weight natural soap base and from about 0 to 60% by weight synthetic soap base. Preferably, the soap base may comprise 50 to 100% by weight natural soap base and 0 to 50% by weight synthetic soap base. More preferably, the soap base may comprise 70 to 100% natural soap base and 0 to 30% by weight synthetic soap base. Where it is desired to form the solid shampoo/soap product of this invention into a solid form other than a flat bar or cake, i.e. such as into a saddle shaped bar or cake, it is preferred that no more than 30% by weight of the soap base be comprised of synthetic soap base since amounts greater than this produce compositions too brittle for molding acceptable solid products into the desired shape.

The soap base will generally comprise from about 70 to about 90% by weight of the total shampoo/soap composition, preferably about 70 to about 85% by weight.

The shampoo/soap composition of this invention will also have present from about 3 to about 15%, preferably about 9 to about 15%, of (A) disodium lauryl sulfosuccinate, sodium cocyl isethionate or sodium lauryl sulfate and from about 2% to about 10%, preferably about 6 to about 10%, of (B) cocoamide MEA, cocoamide DEA or lauramide DEA in which the amount of components (A) and (B) are present in a weight ratio of about 3:2. These components may be present as part of the synthetic detergent soap base or may be added to the natural soap base or to the mixture of natural and synthetic soap bases. These two components, (A) and (B), will thus comprise from about 5 to about 25%, preferably about 15 to about 25%, by weight of the total shampoo/soap composition.

Components (A) and (B) in the 3:2 weight ratio act synergistically as complexing and/or solubilizing agents in the shampoo/soap formulations of this invention and render the natural soap base more soluble and/or substantially eliminates any lime-soap residue or deposit forming and remaining on the hair or scalp. Not only do these components act as complexing agents in the compositions of this invention but they also function as foam boosters and skin and hair conditioning agents.

Thus, the shampoo/soap bar compositions of this invention can be employed as regular skin and body cleansing product and also be used as a shampoo on the hair or scalp, even in hard water areas, without leaving an undesirable residue or deposit on the hair and scalp while providing sufficient and acceptable lathering. Another advantage obtained by the use of such shampoo/soap bar as a hair or scalp shampoo resides in the fact that the user has much greater control over the amount of shampoo to be used. As the user lathers up the hair or scalp, the user can readily perceive when sufficient lathering for his/her purposes has been obtained and simply stop further use of the shampoo/soap bar whereas with prior at liquid, gel, paste and aerosol shampoos, the user would only guess at the amount of shampoo to be discharged from the container therefore was invariably discharging an excess of shampoo that was unnecessary and was essentially wasted.

The shampoo/soap compositions of this invention preferably also includes hair conditioning agents. Any suitable conditioning agent which does not adversely affect the moldability of the shampoo/soap compositions into a solid form and which performs its hair conditioning function without producing an undesirable reside or film on the hair or scalp may be used in the compositions of this invention. For example, the compositions of this invention may have present one or more hair conditioning agents, such as, for example, hydroxy cetyl diammonium phosphate, cocofatty acid, lauryl cocoyl sarcosine, lanolin, isopropyl myristate, butyl palmitate, glycerol, propylene glycol and the like added in effective hair conditioning amounts, generally in an amount up to about 1.5%, preferably about 1.0%, by weight based on the total weight of the shampoo/soap composition.

It is also desirable that a hair conditioning agent which holds the natural oil in the hair and provides a good shine to the hair be included in the compositions. As an example of such an agent there can be mentioned silicone glycol copolymer available from Dow Corning Corporation. However, due to the silicone related antifoam characteristics of the copolymer no more than about 0.75% by weight thereof, based on the total weight of the composition, should be added to the shampoo/soap composition otherwise the lathering action of the product will be unduly inhibited.

Additionally, the shampoo/soap compositions of this invention may contain an agent to provide a skin conditioning effect as well as a hair conditioning effect. For example, a skin conditioning effective amount of skin conditioning agent, such as guar hydroxypropyl trimonium chloride available from the Dehydag division of Henkel Chemicals (Canada) Ltd. as Cosmedia Guar C 261N, can be employed in an amount up to about 1% by weight, preferably at about 0.5% by weight based on the total weight of the shampoo/soap composition.

It is also desirable that the compositions of this invention contain one or more chelating or sequestering agents in amounts effective to complex undesired metal ions in the composition and to prevent lime soap formation. Any suitable such complexing agents may be employed, such as, for example, citric acid, tetrasodium pyrophosphate, tripolyphosphate and the like and salts of ethylenediamine tetraacetic acid, such as, for example, tetrasodium EDTA and HEDTA (hydroxyethylethylenediaminetriacetic acid) and the like.

In addition, the shampoo/soap compositions of this invention may have present any suitable and desirable fragrance, deodorant, coloring agent or dye and preservative or antioxidant. For example, a preservative such as butylated hydroxytoluene (BHT), or butylated hydroxyanisole (BHA) or the like can be added in a preservative effective amount of up to about 0.5%, preferably about 0.25%, by weight based on the total weight of the composition.

As examples of shampoo/soap compositions of this invention which may be molded into bars or cakes, there may be mentioned the following illustrative compositions.

| Component | Formulation No. | | | | |
|---|---|---|---|---|---|
| | 1 | 2 | 3 | 4 | 5 |
| | Amount - % by weight | | | | |
| | Composition | | | | |
| Natural soap base* | 85.50 | 79.75 | 74.75 | 40.00 | 56.00 |
| Synthetic detergent soap base** | — | — | — | 39.75 | 23.75 |
| Disodium lauryl sulfosuccinate | 6.00 | 9.00 | 12.00 | 9.00 | 9.00 |
| Cocoamide MEA | 4.00 | 6.00 | 8.00 | 6.00 | 6.00 |
| Hydroxycetyl diammonium phosphate | 1.00 | 1.00 | 1.00 | 1.00 | 1.00 |
| Fragrance | 1.00 | 1.00 | 1.00 | 1.00 | 1.00 |
| Dimethicone copolyol | 0.75 | 0.75 | 0.75 | 0.75 | 0.75 |
| Cosmedia Guar C 261N | 0.50 | 0.50 | 0.50 | 0.50 | 0.50 |
| Cocofatty acid | 0.50 | 0.50 | 0.50 | 0.50 | 0.50 |
| Deodorant | 0.25 | 0.25 | 0.25 | 0.25 | 0.25 |
| Tetrasodium etidronate | 0.25 | 0.25 | 0.25 | 0.25 | 0.25 |
| HEDTA | 0.25 | 0.25 | 0.25 | 0.25 | 0.25 |

-continued

| | Formulation No. | | | | |
|---|---|---|---|---|---|
| Component | 1 | 2 | 3 | 4 | 5 |
| | Amount - % by weight | | | | |
| Coloring agent | q.s. | q.s. | q.s. | q.s. | q.s. |

*Natural soap base is saponified coconut oil
**Synthetic soap base comprises sodium lauryl sulfate, disodium monolauryl sulfosuccinate, cetearyl alcohol, corn starch, sodium sulfate and water.

To prepare shampoo/soap bars or cakes of this invention, the ingredients of a formulation are mixed together in a mixer, such as a ribbon mixer, and after uniform mixing the mixture is put through a refiner one or more times to obtain product uniformity and then the mixture is extruded under pressure into molds of the desired shape to form cakes or bars of the shampoo/soap product.

What is claimed is :

1. A composition suitable for molding into a solid product useful both as a shampoo for the hair or scalp and as a cleansing agent for the skin or body comprising:
   (A) from about 70% to about 90% by weight of the composition of a soap base selected from a natural soap base or a mixture of a natural soap base and a synthetic detergent soap base wherein the synthetic detergent soap base may be present in an amount up to about 60% by weight based on the combined weight of the natural and synthetic detergent soap bases, and
   (B) from about 5 to about 25% by weight of the composition of:
      (1) a compound selected from the group consisting of disodium lauryl sulfosuccinate, sodium cocyl isethionate or sodium lauryl sulfate, and
      (2) a compound selected from the group consisting of cocoamide monoethanolamide, cocoamide diethanolamide or lauramide diethanolamide,
   wherein the weight ratio of the compounds from Components (1) and (2) in the composition is about 3:2.

2. A composition of claim 1 wherein Component (1) is disodium lauryl sulfosuccinate and Component (2) is cocoamide monoethanolamide.

3. A composition of claim 1 wherein components (1) and (2) are present in an amount of about 9% to about 15% of component (1) and from about 6% to about 10% of component (2).

4. A composition of claim 2 wherein components (1) and (2) are present in an amount of about 9% to about 15% of component (1) and from about 6% to about 10% of component (2).

5. A composition of claim 1 also having present a hair conditioning effective amount of a hair conditioning agent.

6. A composition of claim 2 also having present a hair conditioning effective amount of a hair conditioning agent.

7. A composition of claim 4 also having present a hair conditioning effective amount of a hair conditioning agent.

8. A composition of claim 1 also having present a skin conditioning effective amount of a skin conditioning agent.

9. A composition of claim 2 also having present a skin conditioning effective amount of a skin conditioning agent.

10. A composition of claim 7 also having present a skin conditioning effective amount of a skin conditioning agent.

11. A composition of claim 1 wherein the soap base is a natural soap base of saponified coconut oil.

12. A composition of claim 7 wherein the soap base is a natural soap base of saponified coconut oil.

13. A composition of claim 10 wherein the soap base is a natural soap base of saponified coconut oil.

14. A composition of claim 1 in the shape of a bar or cake.

15. A composition of claim 2 in the shape of a bar or cake.

16. A composition of claim 6 in the shape of a bar or cake.

17. A composition of claim 7 in the shape of a bar or cake.

18. A composition of claim 9 in the shape of a bar or cake.

19. A composition of claim 10 in the shape of a bar or cake.

20. A composition of claim 11 in the shape of a bar or cake.

21. A composition of claim 12 in the shape of a bar or cake.

22. A compsition of claim 13 in the shape of a bar or cake.

23. A solid bar or cake composition useful both as a shampoo for the hair or scalp and as a cleansing agent for the skin or body comprising:
   from about 70% to about 90% by weight of the composition of a soap selected from a natural soap base or a mixture of a natural soap base and a synthetic detergent soap base wherein the synthetic detergent soap base may be present in an amount up to about 60% by weight based on the combined weight of the natural and synthetic detergent soap bases,
   from about 3 to about 15% by weight of disodium lauryl sulfosuccinate and from about 2 to about 10% by weight of cocoamide monoethanolamide with the proviso that the weight ratio of disodium lauryl sulfosuccinate to cocoamide monoethanolamide is about 3:2,
   a hair conditioning effective amount of a hair conditioning agent,
   a skin conditioning effective amount of a skin conditioning agent,
   a sequestering agent in a metal complexing effective amount, and
   an antioxidant effective amount of an anitoxidant.

24. A solid bar or cake composition useful both as a shampoo for the hair or scalp and as a cleansing agent for the skin or body comprising:

| Component | [Formulation No. 1] % by weight |
|---|---|
| Natural soap base | 85.50 |
| Disodium lauryl sulfosuccinate | 6.00 |
| Cocoamide [MEA] monoethanolamide | 4.00 |
| Hydroxycetyl diammonium phosphate | 1.00 |
| Fragrance | 1.00 |
| Dimethicone copolyol | 0.75 |
| Cosmedia Guar C 261N | 0.50 |
| Cocofatty acid | 0.50 |
| Deodorant | 0.25 |
| Tetrasodium etidronate | 0.25 |
| [HEDTA] Hydroxyethylethylenediaminetriacetic acid | 0.25 |

-continued

| Component | [Formulation No. 1] % by weight |
|---|---|
| Coloring agent | q.s. |

25. A solid bar or cake composition useful both as a shampoo for the hair or scalp and as a cleansing agent for the skin or body comprising:

| Component | [Formulation No. 3] % by weight |
|---|---|
| Natural soap base | 74.75 |
| Disodium lauryl sulfosuccinate | 12.00 |
| Cocoamide [MEA] monoethanolamide | 8.00 |
| Hydroxycetyl diammonium phosphate | 1.00 |
| Fragrance | 1.00 |
| Dimethicone copolyol | 0.75 |
| Cosmedia Guar C 261N | 0.50 |
| Cocofatty acid | 0.50 |
| Deodorant | 0.25 |
| Tetrasodium etidronate | 0.25 |
| [HEDTA] Hydroxyethylethylenediamine-triacetic acid | 0.25 |
| Coloring agent | q.s. |

26. A solid bar or cake composition useful both as a shampoo for the hair or scalp and as a cleansing agent for the skin or body comprising:

| Component | [Formulation No. 4] % by weight |
|---|---|
| Natural soap base | 40.00 |
| Synthetic detergent soap base | 39.75 |
| Disodium lauryl sulfosuccinate | 9.00 |
| Cocoamide [MEA] monoethanolamide | 6.00 |
| Hydroxycetyl diammonium phosphate | 1.00 |
| Fragrance | 1.00 |
| Dimethicone copolyol | 0.75 |
| Cosmedia Guar C 261N | 0.50 |
| Cocofatty acid | 0.50 |
| Deodorant | 0.25 |
| Tetrasodium etidronate | 0.25 |
| [HEDTA] Hydroxyethylethylenediamine-triacetic acid | 0.25 |
| Coloring agent | q.s. |

27. A composition of claim 1 wherein the synthetic detergent soap base comprises a detergent selected from the group consisting of nonionic and anionic detergents.

28. A composition of claim 27 in the shape of a bar or cake in which a soap residue forming and remaining on the hair or scalp is substantially eliminated when the bar or cake is used as a shampoo.

* * * * *